(12) United States Patent
Sohma et al.

(10) Patent No.: US 9,186,078 B2
(45) Date of Patent: Nov. 17, 2015

(54) OPTICAL FIBER SHEET

(71) Applicants: SUMITOMO ELECTRIC INDUSTRIES, LTD., Osaka-shi, Osaka (JP); Seiko Mitachi, Kunitachi-shi, Tokyo (JP)

(72) Inventors: Kazuyuki Sohma, Yokohama (JP); Kazuhiro Kuwa, Osaka (JP); Toshifumi Hosoya, Osaka (JP); Masumi Ito, Yokohama (JP); Seiko Mitachi, Kunitachi-shi (JP)

(73) Assignees: SUMITOMO ELECTRIC INDUSTRIES, LTD., Osaka-shi, Osaka (JP); Mitachi Seiko, Tokyo ( * ) Notice: Subject to any disclaimer, the term of this patent is extended or adjusted under 35 U.S.C. 154(b) by 0 days.

(21) Appl. No.: 14/349,445

(22) PCT Filed: Oct. 3, 2012

(86) PCT No.: PCT/JP2012/075637
§ 371 (c)(1),
(2) Date: Apr. 3, 2014

(87) PCT Pub. No.: WO2013/051602
PCT Pub. Date: Apr. 11, 2013

(65) Prior Publication Data
US 2014/0270669 A1     Sep. 18, 2014

(30) Foreign Application Priority Data

Oct. 5, 2011    (JP) ................................ 2011-220912

(51) Int. Cl.
*G02B 6/00*        (2006.01)
*A61B 5/00*        (2006.01)
(Continued)

(52) U.S. Cl.
CPC ........... *A61B 5/02444* (2013.01); *A61B 5/0205* (2013.01); *A61B 5/0803* (2013.01);
(Continued)

(58) Field of Classification Search
CPC ........... A61B 5/113; A61B 2562/0266; A61B 5/0205; A61B 5/024; A61B 5/0244; A61B 5/0873; G02B 6/02033; G08B 13/124
USPC ............. 385/12, 13; 600/180, 182, 301, 476, 600/587, 595
See application file for complete search history.

(56) References Cited

U.S. PATENT DOCUMENTS 5,282,258 A *   1/1994   Hoshino ......................... 385/70
5,291,013 A *   3/1994   Nafarrate et al. ......... 250/227.14
(Continued)

FOREIGN PATENT DOCUMENTS

JP     2007-061306 A     3/2007
JP     2007-144070 A     6/2007
(Continued)

OTHER PUBLICATIONS

English-language translation of International Preliminary Report on Patentability (IPRP) dated Apr. 17, 2014 that issued in WO Patent Application No. PCT/JP2012/075637.

*Primary Examiner* — Robert Tavlykaev
(74) *Attorney, Agent, or Firm* — Drinker Biddle & Reath LLP (57) ABSTRACT

An optical fiber sheet 10 includes an optical fiber 11 and a wire 12 that are arranged between a first sheet and a second sheet. The optical fiber 11 is a multi-mode optical fiber having a core of silica glass to which a refractive index adjuster is added, has a numerical aperture equal to or less than 0.30 and a flexural rigidity equal to or less than $0.50\,N\cdot mm^2$, and is bent to be arranged between the first sheet and the second sheet. The wire 12 intersects the optical fiber 11 between the first sheet and the second sheet.

5 Claims, 8 Drawing Sheets (51) Int. Cl.
*A61B 5/103* (2006.01)
*A61B 5/117* (2006.01)
*A61B 5/024* (2006.01)
*G02B 6/02* (2006.01)
*A61B 5/0205* (2006.01)
*A61B 5/08* (2006.01)
*A61B 5/087* (2006.01)
*G02B 6/12* (2006.01)

(52) U.S. Cl.
CPC ............ *A61B5/0826* (2013.01); *A61B 5/0873* (2013.01); *G02B 6/02033* (2013.01); *A61B 2562/0266* (2013.01); *G02B 2006/12138* (2013.01)

(56) References Cited

U.S. PATENT DOCUMENTS

| | | | |
|---|---|---|---|
| 2003/0012536 A1* | 1/2003 | Simomichi et al. | 385/128 |
| 2003/0095263 A1* | 5/2003 | Varshneya et al. | 356/477 |
| 2012/0134670 A1* | 5/2012 | Hamada | 398/43 |
| 2012/0203117 A1* | 8/2012 | Chen et al. | 600/484 |

FOREIGN PATENT DOCUMENTS

| | | |
|---|---|---|
| JP | 2008-206908 A | 9/2008 |
| JP | 2008-284001 A | 11/2008 |
| JP | 2010-131340 A | 6/2010 |
| JP | 2012-065911 A | 4/2012 |

* cited by examiner

OPTICAL FIBER SHEET

TECHNICAL FIELD

The present invention relates to an optical fiber sheet.

BACKGROUND ART

Techniques using an optical fiber sheet as a breathing sensor are disclosed in Patent Literatures 1 to 3. An optical fiber sheet disclosed in Patent Literature 1 is formed by fixing or mixing an optical fiber to/into a sheet made of cloth or the like. This optical fiber sheet captures a shape change of the optical fiber that is produced by a body motion, as a change in polarization state of light propagating through the optical fiber. It is said that, when using this optical fiber sheet, the S/N ratio is good, a slight body motion produced by breathing can be detected, turning over and breathing can be clearly distinguished, and a respiratory status in a circumstance close to a normal living environment can be observed.

Patent Literatures 2 and 3 disclose a sleep apnea sensor that enables screening of sleep apnea syndrome in a normal sleep state completely without constraint at home. This sleep apnea sensor detects a body motion by measuring a change in light quantity of transmission light based on an excessive loss produced by a lateral pressure applied on the optical fiber. This sleep apnea sensor is small and silent, can be used by simply lying on an optical fiber sheet laid under a sheet covering the bedding, and can perform a measurement with nothing on the body and with a simple operation. The optical fiber sheets disclosed in these literatures can observe a state of breathing in a circumstance close to a normal living environment.

CITATION LIST

Patent Literature

Patent Literature 1: Japanese Patent Application Laid-Open
Publication No. 2007-61306
Patent Literature 2: Japanese Patent Application Laid-Open Publication No, 2007-144070
Patent Literature 3: Japanese Patent Application Laid-Open Publication No. 2010-131340

SUMMARY OF INVENTION

Technical Problem

The optical fiber sheets disclosed in Patent Literatures 1 to 3 have enough sensitivity to measure breathing but do not have sensitivity high enough to measure heartbeats. Patent Literatures 1 to 3 imply heartbeat measurement using the optical fiber sheets but do not describe any example of heartbeat measurement, The present invention is made to solve the aforementioned problem and aims to provide an optical fiber sheet having high sensitivity and being capable of heartbeat measurement,

Solution to Problem

An optical fiber sheet according to the present invention includes an optical fiber and a wire that are arranged between a first sheet and a second sheet. in this optical fiber sheet, the optical fiber is a multi-mode optical fiber having a core of silica glass to which a refractive index adjuster is added, has a numerical aperture equal to or less than 0.30 and a flexural rigidity equal to or less than 0.50 N·mm$^2$, and is bent to be arranged between the first sheet and the second sheet. The wire intersects the optical fiber between the first sheet and the second sheet, In the optical fiber sheet according to the present invention, it is preferable that a flexural rigidity of the wire be equal to or greater than the flexural rigidity of the optical fiber, It is preferable that the optical fiber have the core having a diameter of 20 to 130 μm and a clad provided around the core, and the clad be made of resin and have a thickness of 10 to 40 μm.

Advantageous Effects of Invention

The optical fiber sheet according to the present invention has high sensitivity and is capable of heartbeat measurement.

DESCRIPTION OF EMBODIMENTS

Embodiments for carrying out the invention will be described in details below with reference to the accompanying drawings. In the description of the drawings, the same elements are denoted with the same reference signs, and an overlapping description is omitted.

Figure 1:
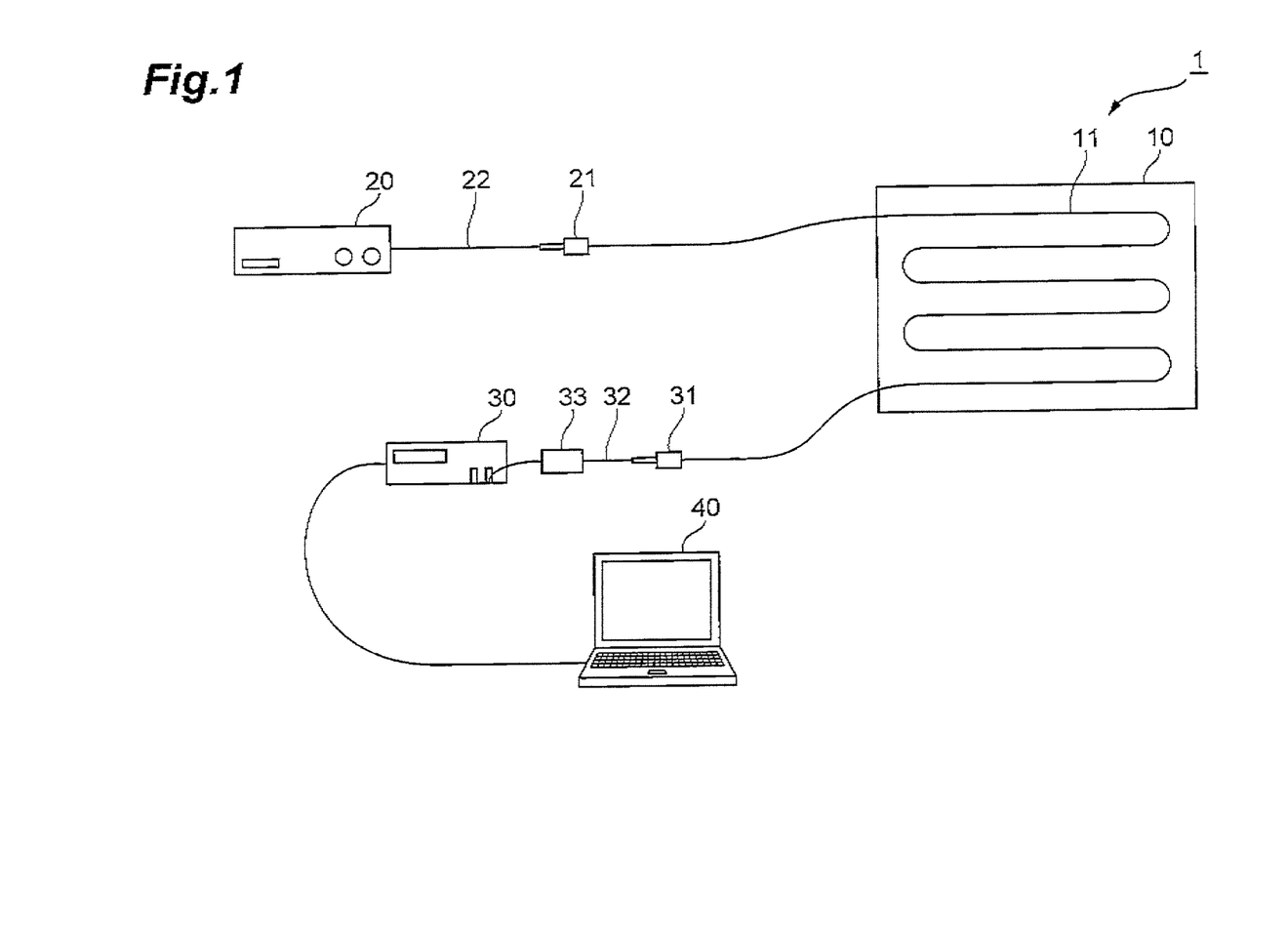
FIG. 1 is a diagram showing a configuration of a measurement system 1 including an optical fiber sheet 10 of the present embodiment

FIG. 1 is a diagram showing a configuration of a measurement system 1 including an optical fiber sheet 10 of the present embodiment, The measurement system 1 includes the optical fiber sheet 10, a light source unit 20, a detector 30, and an analysis unit 40, The optical fiber sheet 10 includes an optical fiber 11 and a wire arranged between a first sheet and a second sheet. The optical fiber 11 is a multi-mode optical fiber having a core of silica glass to which a refractive index adjuster is added, and is bent to be arranged between the first sheet and the second sheet. The details of the optical fiber sheet 10 will be described later.

The light source unit 20 continuously outputs light at a constant intensity, Light output from the light source unit 20 propagates through an optical fiber 22 and then enters the input end of the optical fiber 11 connected to an optical connector 21 provided at a tip end of the optical fiber 22. The light source unit 20 preferably outputs light from a light-emitting diode or a laser diode.

A light-receiving element 33 receives light exiting from the output end of the optical fiber 11 and reaching there through an optical connector 31 and an optical fiber 32, and outputs a current signal having a value in accordance with the received light intensity, The detector 30 receives the current signal output from the light-receiving element 33, converts the current signal into a voltage signal, and amplifies the voltage signal for output. A silicon photodiode is preferably used as the light-receiving element 33.

The analysis unit 40 receives the voltage signal output from the detector 30, analog-to-digital converts (AD-converts) the voltage signal (analog signal) into a digital signal, and stores and analyzes the digital signal. The analysis unit 40 also displays the digital signal or displays a result obtained by analyzing the digital signal. A personal computer is preferably used as the analysis unit 40.

Figure 2:
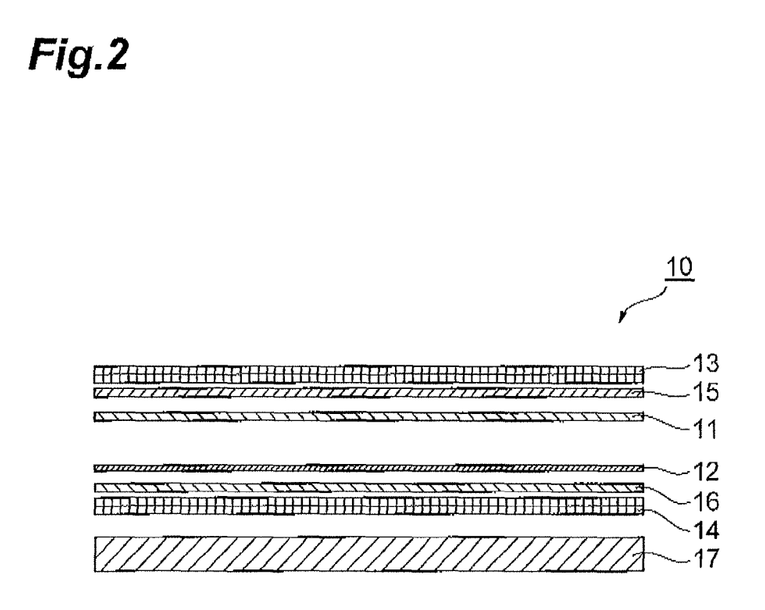
FIG. 2 is a diagram showing a stack structure of the optical fiber sheet 10 of the present embodiment.

FIG. 2 is a diagram showing a stack structure of the optical fiber sheet 10 of the present embodiment. The optical fiber sheet 10 includes the optical fiber 11 and a wire 12 arranged between the first sheet 13 and the second sheet 14.

The optical fiber 11 is a multi-mode optical fiber having a core of silica glass to which a refractive index adjuster (for example, $GeO_2$) is added. The numerical aperture of the optical fiber 11 is equal to or less than 0.30. The flexural rigidity of the optical fiber 11 is equal to or less than 0.50 N·mm². The optical fiber 11 is bent to be arranged between the first sheet 13 and the second sheet 14.

When the Young's modulus of the i-th layer is $G_i$ and the sectional secondary moment of the i-th layer is $I_i$, the flexural rigidity D is expressed by the equation:

$$D=\Sigma(G_i \times I_i).$$

In a case where a center layer has a column shape and each of the other layers has a cylindrical shape as in an optical fiber, when the outer diameter of the i-th layer is the sectional secondary moment $I_i$ of the i-th layer is expressed by the equation:

$$I_i=\pi(R_i^4-R_{i-1}^4)/64.$$

The optical fiber 11 having the numerical aperture and the flexural rigidity as described above can be designed to have the core having a diameter of 20 to 130 μm, preferably 20 to 100 μm, and a clad provided around the core. The clad is made of resin and can be designed to have a thickness in a range of 10 to 40 μm. The refractive index distribution of the core may be approximately uniform or may be of the GI (Graded Index) type in which the refractive index is higher toward the center. The resin that forms the clad is, for example, an ultraviolet curable resin, such as acrylate fluoride, The optical fiber having a clad formed of such a resin is called HPCF (Hard Plastic Clad Silica Fiber).

The optical fiber 11 may be used in a state in which the outermost layer is a clad (for example, an outer diameter of 125 μm). Alternatively, the optical fiber 11 may be used in a state in which an ultraviolet curable resin is further provided around the clad (for example, an outer diameter of 250 μm).

The wire 12 intersects the optical fiber 11 between the first sheet 13 and the second sheet 14. "Intersect" means that the optical fiber 11 and the wire 12 intersect each other as viewed from the direction vertical to the plane of the sheets 13 and 14 and that the wire 12 may apply a lateral pressure on the optical fiber 11 when force is externally applied in the vertical direction. The optical fiber 11 causes microbending loss when given a lateral pressure. The greater the number of intersections between the optical fiber 11 and the wire 12, the more preferable.

A plurality of wire 12 may be provided, or one or more wires 12 may be bent to be arranged, The optical fiber 11 may also serve as the wire 12 (in this case, the flexural rigidity of the wire 12 is equivalent to the flexural rigidity of the optical fiber 11). The wire 12 may be an optical fiber different from the optical fiber 11 or may be a wire of a metal having relatively high flexural rigidity. In order to effectively apply a lateral pressure to the optical fiber 11, it is preferable that the flexural rigidity of the wire 12 should be greater than the flexural rigidity of the optical fiber 11. The outer diameter of the wire 12 is, for example, 250 to 500 μm.

The optical fiber 11 is fixed to the first sheet 13 with a double-sided adhesive tape 15. The first sheet 13 supports the optical fiber 11. The wire 12 is fixed to the second sheet 14 with a double-sided adhesive tape 16. The second sheet 14 supports the wire 12.

The first sheet 13 and the second sheet 14 not only may be cloth (woven fabric, knitted fabric, nonwoven fabric, or the like) but also may be a variety of sheets such as a plastic sheet, paper, net cloth having a mesh structure, and a sponge sheet, The sheets 13 and 14 are preferably net sheets having a breathable mesh structure having a number of voids.

For example, when the optical fiber sheet 10 is put into a bag made of cloth (for example, made of cotton) to be used, a non-slip sheet 17 provided under the second sheet 14 is provided to prevent the optical fiber sheet 10 from slipping and moving in the bag. The optical fiber sheet 10 in this manner is laid, for example, on a bed and used to measure breathing and heartbeats of a subject lying thereon.

Figure 3:
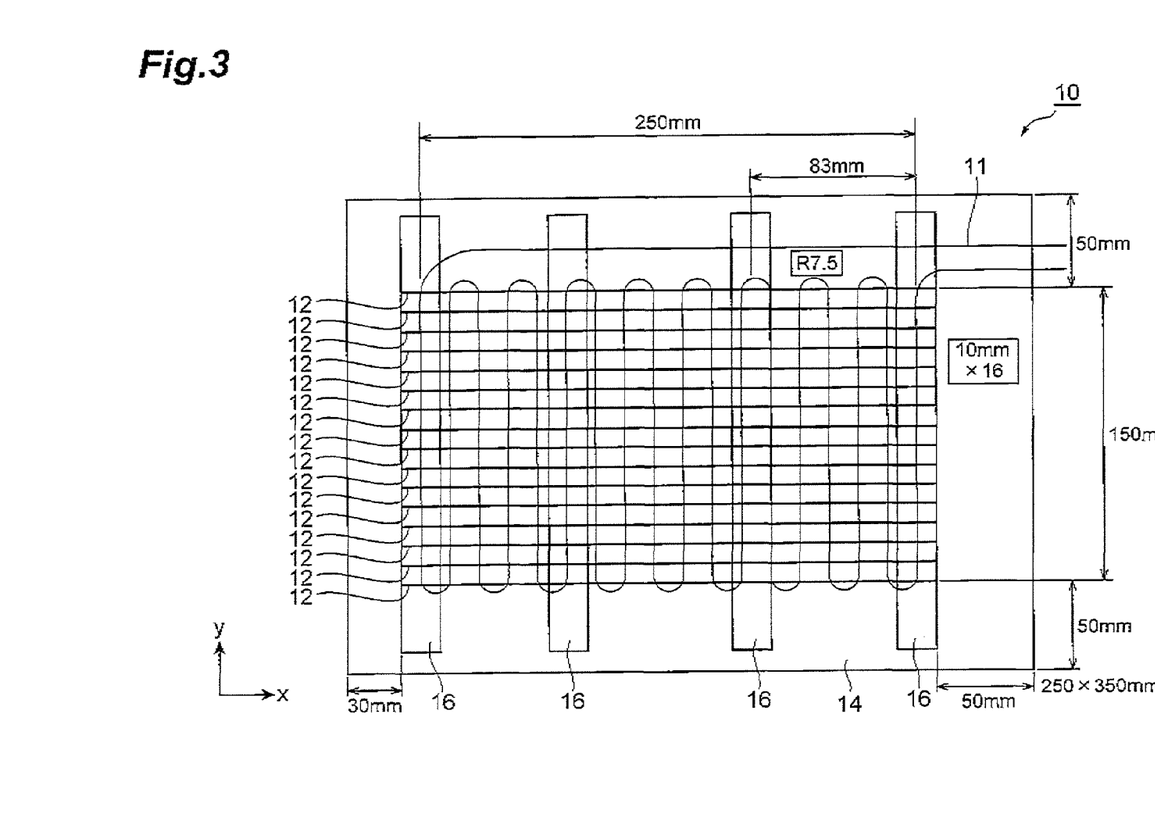
FIG. 3 is a diagram showing a planar structure of the optical fiber sheet 10 of the present embodiment.

FIG. 3 is a diagram showing a planar structure of the optical fiber sheet 10 of the present embodiment, This figure particularly shows the planar structure of the optical fiber 11, the wire 12, the double-sided adhesive tape 16, and the second sheet 14. In this figure, an xy orthogonal coordinate system is shown for the sake of convenience of explanation, This figure also shows specific shape and sizes regarding Examples and Comparative Example described later.

In a configuration example shown in the figure, four double-sided adhesive tapes 16 extending in the y direction are provided on the rectangular second sheet 14 with an x-direction size of 350 mm and a y-direction size of 250 mm. The four double-sided adhesive tapes 16, each having an x-direction width of 20 mm, are provided at regular intervals with an x-direction pitch of 83 mm. Sixteen wires 12, each extending in the x direction, are provided at regular intervals with a y-direction pitch of 10 mm on the four double-sided adhesive tapes 16.

The optical fiber 11 is bent a number of times to have an x-direction pitch of 15 mm and is arranged to extend over an x-direction width of 250 mm. The radius of curvature of each bend of the optical fiber 11 is 7.5 mm. A straight portion from one bend to another bend of the optical fiber 11 extends in the y direction with a length of 150 mm and intersects the sixteen wires 12.

The measurement system 1 including the optical fiber sheet 10 configured as described above operates as follows, Light at a constant intensity continuously output from the light source unit 20 passes through the optical fiber 22 and the optical connector 21 and enters the input end of the optical fiber 11. Light entering the input end is propagated by the optical fiber 11 and thereafter exits from the output end of the optical fiber 11. Light exiting from the output end passes through the optical connector 31 and the optical fiber 32 and is received by the light-receiving element 33, A current signal having a value in accordance with the received light intensity is output from the light-receiving element 33, In the detector 30, the current signal output from the light-receiving element 33 is input, the current signal is converted into a voltage signal, the voltage signal is amplified, the voltage signal (analog signal) is AD-converted into a digital signal, and the digital signal is transmitted to the analysis unit 40 to be stored and analyzed.

The intensity of light entering the input end of the optical fiber 11 is constant, whereas the intensity of light exiting from the output end of the optical fiber 11 varies in accordance with microbending loss caused by a lateral pressure applied to the optical fiber 11 by the wire 12. The lateral pressure applied to the optical fiber 11 by the wire 12 also varies in accordance with body motions such as breathing, heartbeats, and turning over of the subject lying on the optical fiber sheet 10. Therefore, the time-series voltage signal or digital signal (hereinafter referred to as "light intensity signal") transmitted and recorded in the analysis unit 40 is analyzed (for example, Fourier analysis) whereby body motions such as breathing, heartbeats, and turning over of the subject can be measured. Since breathing and heartbeats have periodicity, the magnitude of the lateral pressure applied to the optical fiber 11 by the wire 12 periodically changes, and thus the magnitude of the light intensity signal periodically changes.

The optical fiber sheets 10 were prototyped using a variety of optical fibers 11, The results of measurement of breathing and heartbeats of a subject using the prototyped optical fiber sheets 10 will now be described. The flexural rigidity of the wire 12 was 1 N·mm².

In Example 1, the one used as the optical fiber 11 was HPCF with a core diameter of 80 μm and a resin clad diameter of 125 μm. The resin clad was the outermost layer. This optical fiber had a numerical aperture NA of 0.30 and a flexural rigidity of 0.16 N·mm².

In Example 2, the one used as the optical fiber 11 was HPCF with a core diameter of 80 μm and a resin clad diameter of 125 μm. The diameter of an ultraviolet curable resin layer provided around the resin clad was 250 μm. This optical fiber had a numerical aperture NA of 0.30 and a flexural rigidity of 0.26 N·mm².

In Example 3, the one used as the optical fiber 11 was HPCF with a core diameter of 50 μm and a resin clad diameter of 125 μm. The diameter of an ultraviolet curable resin layer provided around the resin clad was 250 μm. This optical fiber had a numerical aperture NA of 0.21 and a flexural rigidity of 0.14 N·mm².

In Example 4, the one used as the optical fiber 11 was HPCF with a core diameter of 80 μm and a resin clad diameter of 125 μm.

The diameter of an ultraviolet curable resin layer provided around the resin clad was 250 μm. This optical fiber had a numerical aperture NA of 0.21 and a flexural rigidity of 0.26 N·mm².

In Example 5, the one used as the optical fiber 11 was HPCF with a core diameter of 100 μm and a resin clad diameter of 125 μm.

The diameter of an ultraviolet curable resin layer provided around the resin clad was 250 μm. This optical fiber had a numerical aperture NA of 0.21 and a flexural rigidity of 0.50 N·mm².

In Comparative Example, the one used as the optical fiber 11 was a general multi-mode optical fiber with a core diameter of 50 μm and a glass clad diameter of 125 μm. The diameter of an ultraviolet curable resin layer provided around the clad was 250 μm. This optical fiber had a numerical aperture NA of 0.21 and a flexural rigidity of 0.96 N·mm².

Figure 4:
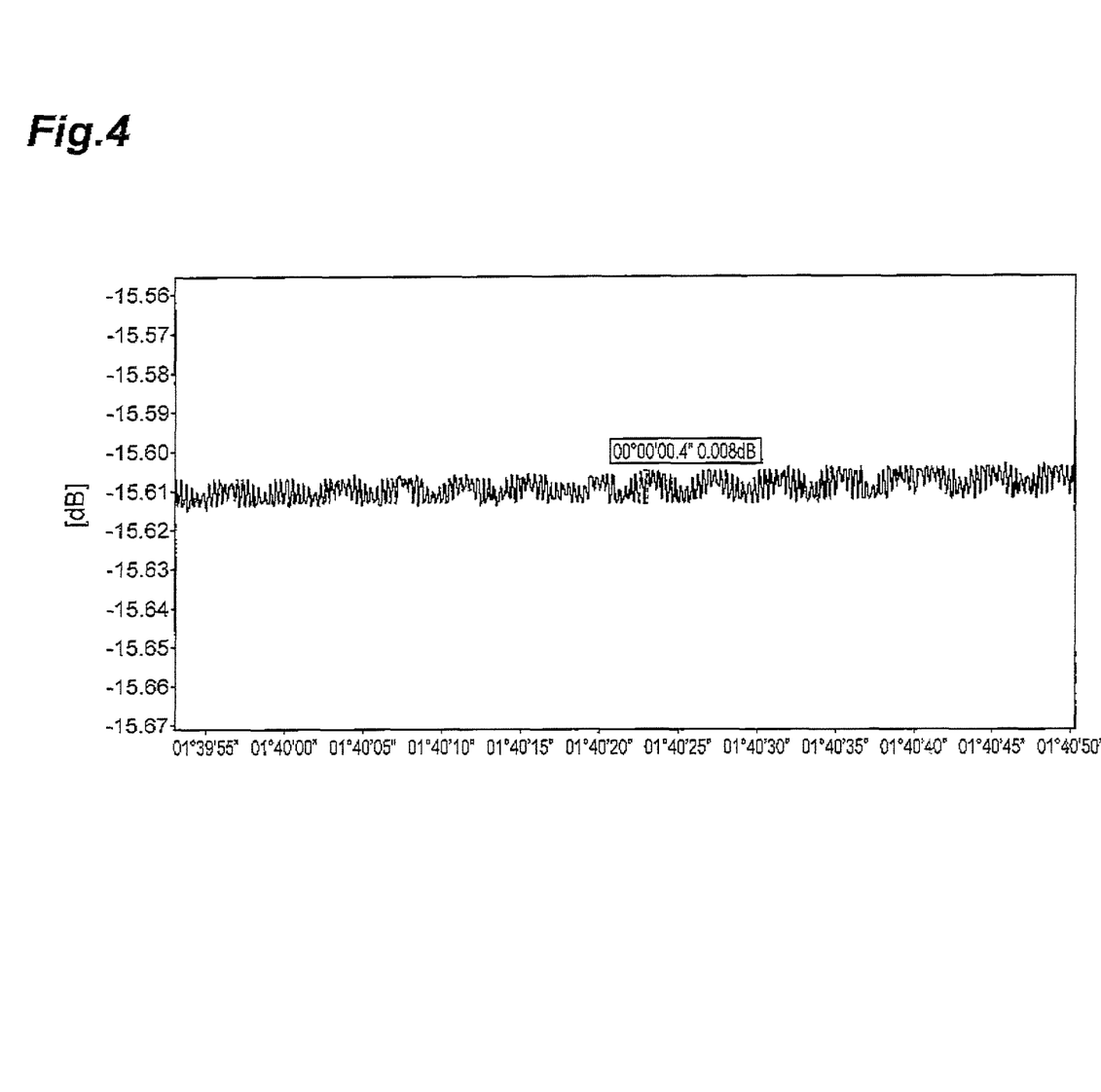
FIG. 4 is a chart showing a light intensity signal obtained by an analysis unit 40 in Example 1.
Figure 5:
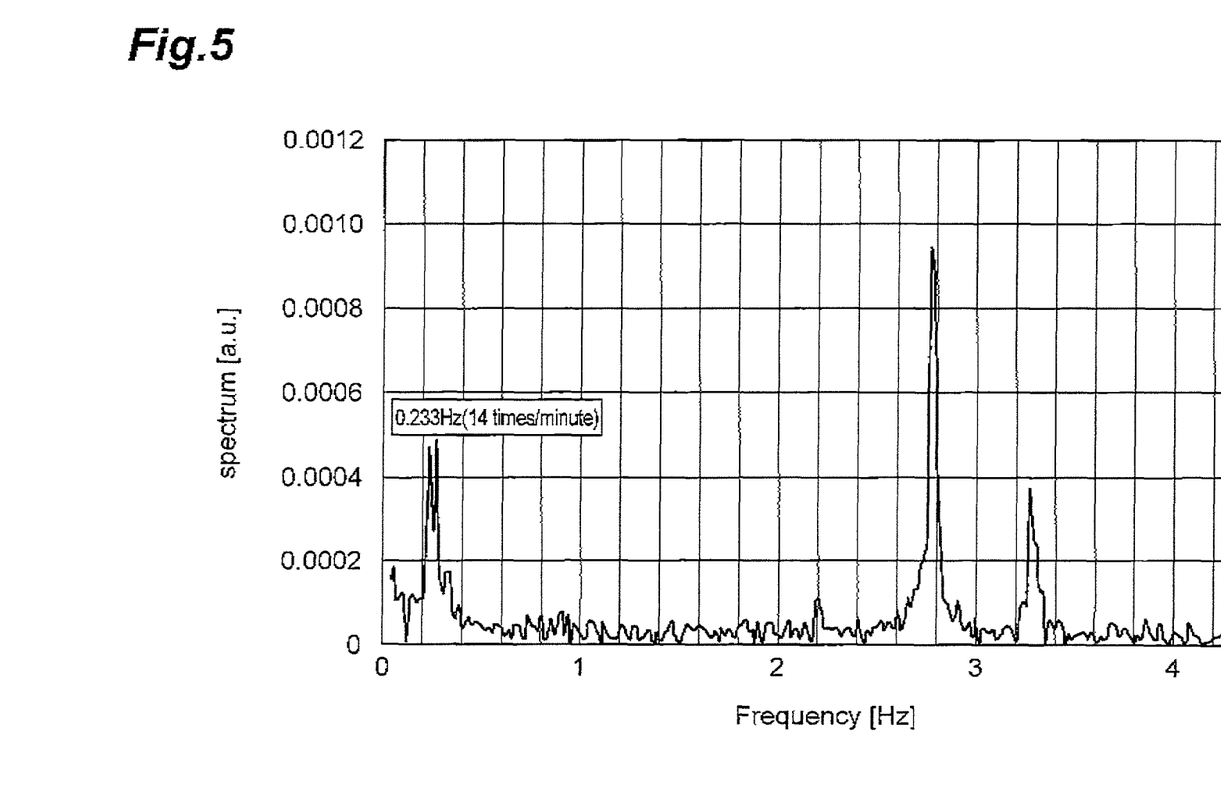
FIG. 5 is a chart showing a result of Fourier transform of the light intensity signal obtained by the analysis unit 40 in Example 1.
Figure 6:
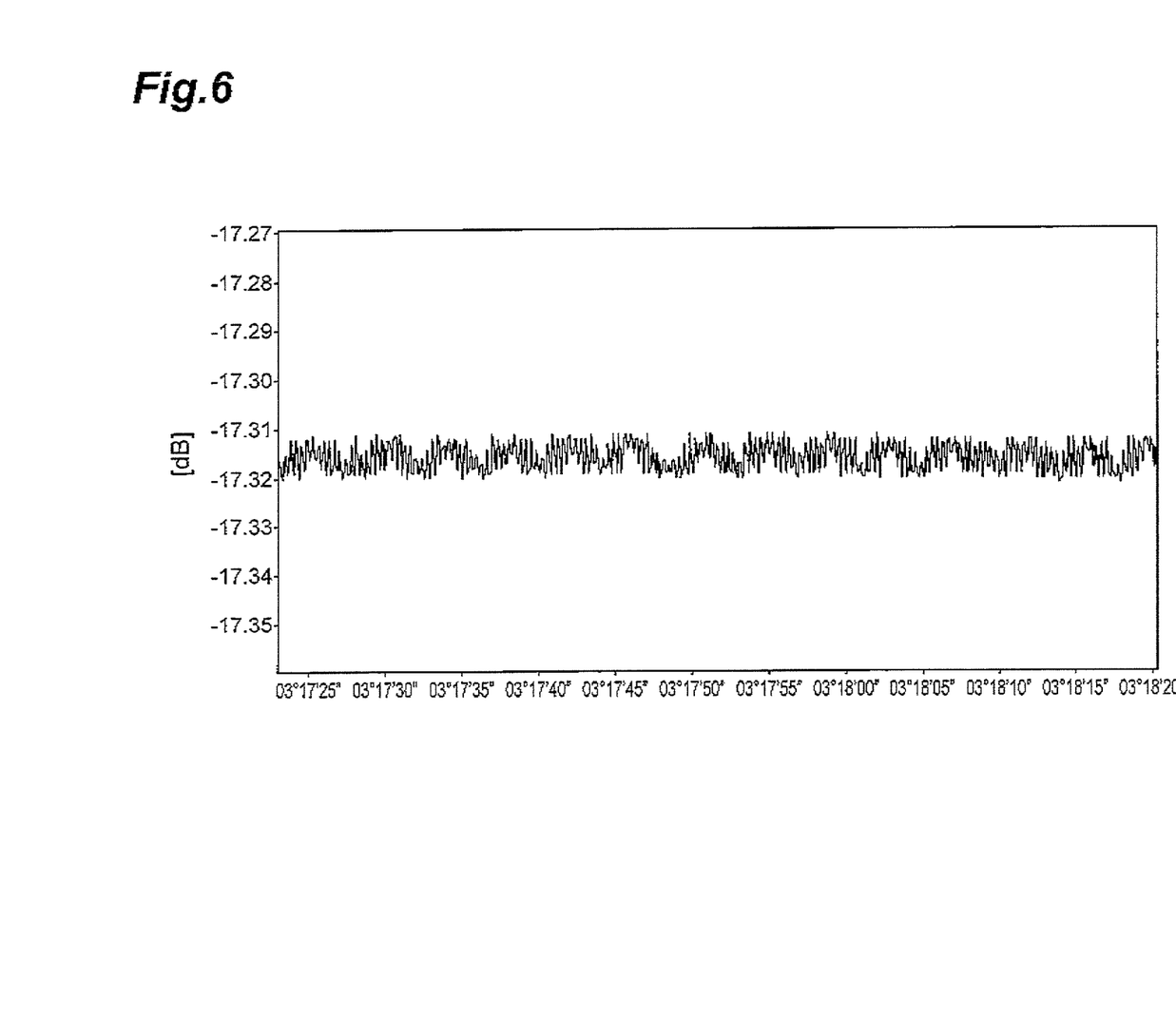
FIG. 6 is a chart showing a light intensity signal obtained by the analysis unit 40 in Example 2.
Figure 7:
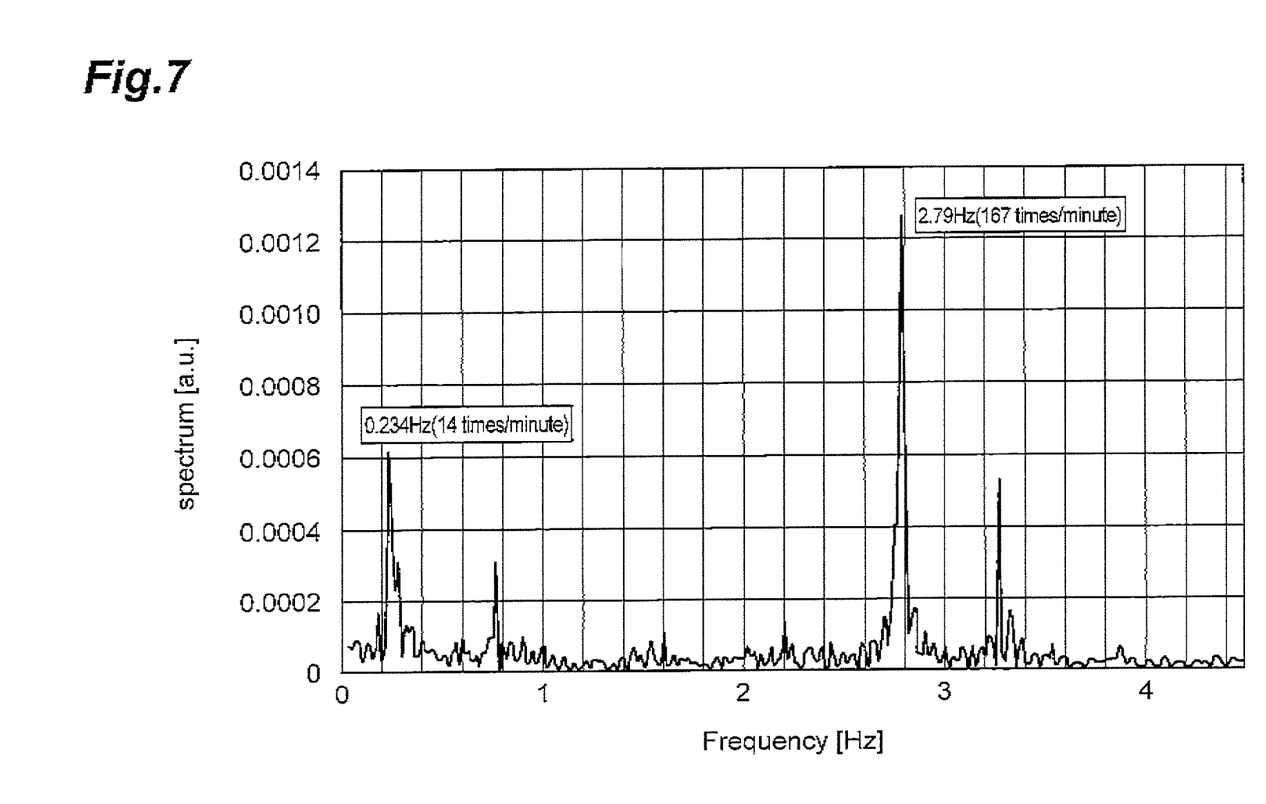
FIG. 7 is a chart showing a result of Fourier transform of the light intensity signal obtained by the analysis unit 40 in Example 2.
Figure 8:
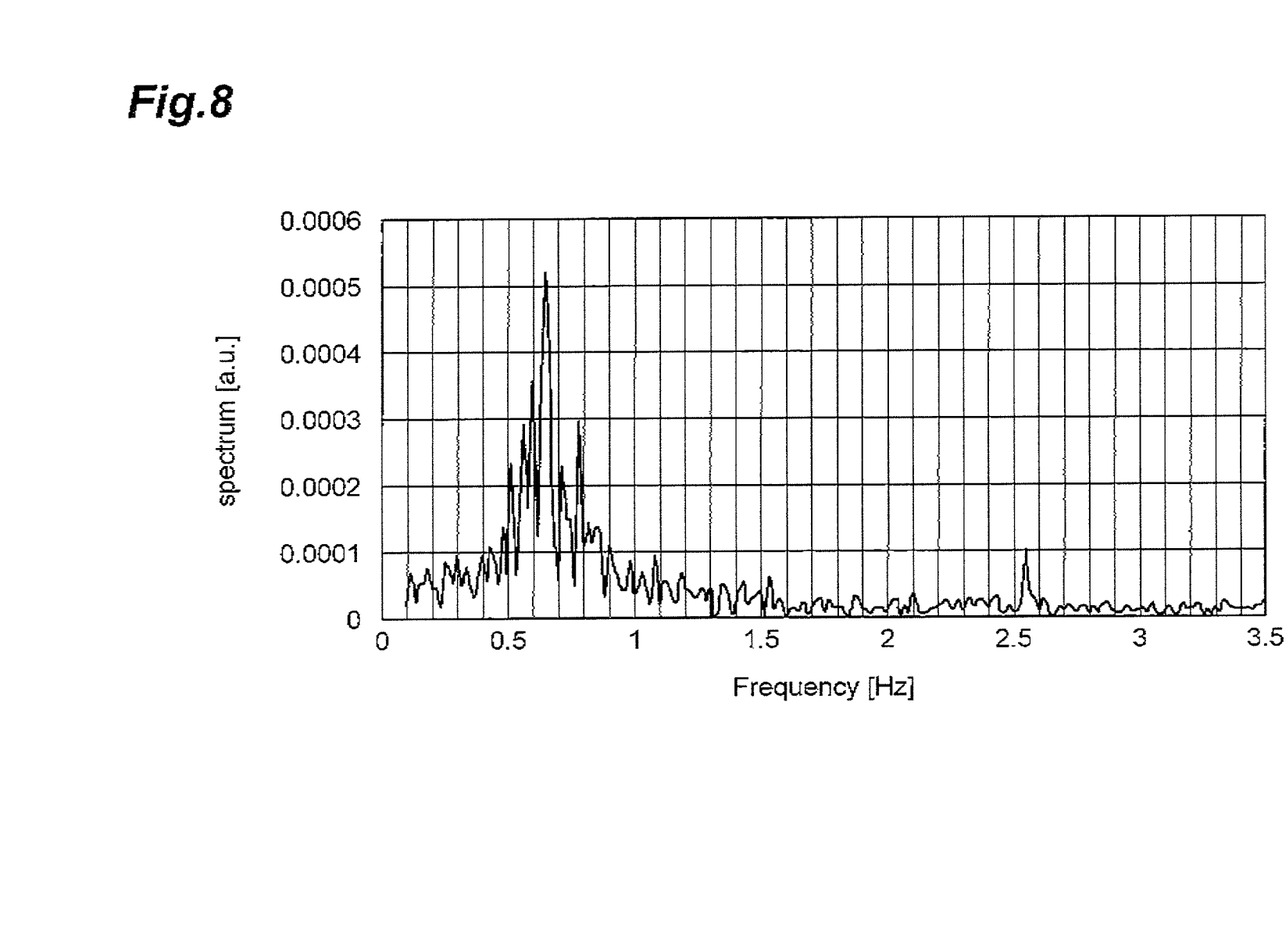
FIG. 8 is a chart showing a result of Fourier transform of a light intensity signal obtained by the analysis unit 40 in Comparative Example.

FIG. 4 is a chart showing a light intensity signal obtained by the analysis unit 40 in Example 1. FIG. 5 is a chart showing a result of Fourier transform of the light intensity signal obtained by the analysis unit 40 in Example 1. FIG. 6 is a chart showing a light intensity signal obtained by the analysis unit 40 in Example 2. FIG. 7 is a chart showing a result of Fourier transform of the light intensity signal obtained by the analysis unit 40 in Example 2. FIG. 8 is a chart showing a result of Fourier transform of a light intensity signal obtained by the analysis unit 40 in Comparative Example. In the charts of the light intensity signal in FIGS. 4 and 6, the abscissa indicates time, and the ordinate indicates the received light intensity of the light-receiving element 33, In the charts of the Fourier transform result in FIGS. 5, 7, and 8, the abscissa indicates frequency, and the ordinate indicates the magnitude of each frequency component, As can be understood from FIGS. 4 to 7, in both Example 1 and Example 2, it was recognized that both a long-period component of breathing and a short-period component of heartbeats clearly existed in the light intensity signal, and not only breathing (in the vicinity of 0.23 Hz) but also heartbeats (in the vicinity of 2.8 Hz) of a subject can be measured. In Example 3, Example 4, and Example 5, not only breathing but also heartbeats of a subject can be measured. In contrast, as can be understood from FIG. 8, in Comparative Example, measurement of heartbeats of a subject was difficult.

The optical fiber sheets 10 were made of other varieties of optical fibers 11 and evaluated. As a result, it was confirmed that when the optical fiber 11 used in the optical fiber sheet 10 is a multi-mode optical fiber having a core of silica glass to which a refractive index adjuster is added, and has a numerical aperture equal to or less than 0.30 and a flexural rigidity equal to or less than 0.50 N·mm², the measurement system 1 including this optical fiber sheet 10 had enough sensitivity to be able to measure not only breathing but also heartbeats of a subject.

REFERENCE SIGNS LIST

1 . . . measurement system, 10 . . . optical fiber sheet, 11 . . . fiber, 12 . . . wire, 13 . . . first sheet, 14 . . . second sheet, 15 . . . double-sided adhesive tape, 16 . . . double-sided adhesive tape, 17 . . . non-slip sheet, 20 . . . light source unit, 21 . . . optical connector, 22 . . . optical fiber, 30 . . . detector, 31 . . . optical connector, 32 . . . optical fiber, 33 . . . light-receiving element, 40 . . . analysis unit.

The invention claimed is:

1. An optical fiber sheet comprising an optical fiber and a wire that are arranged between a first sheet and a second sheet,
   wherein the optical fiber is a multi-mode optical fiber having a core of silica glass to which a refractive index adjuster is added, has a numerical aperture equal to or less than 0.30 and a flexural rigidity equal to or less than 0.50 N ·mm², wherein the optical fiber has the core having a diameter of 20 to 130 μm and a clad provided around the core, and wherein the clad is made of resin and has a thickness of 10 to 40 μm,
   wherein the optical fiber is bent to be arranged between the first sheet and the second sheet, and
   wherein the wire intersects the optical fiber between the first sheet and the second sheet, and a flexural rigidity of the wire is equal to or greater than the flexural rigidity of the optical fiber.

2. The optical fiber sheet according to claim 1,
   wherein the core diameter is 80 μm, the cladding thickness is 22.5 μm and the flexural rigidity of the optical fiber is 0.16 N·mm².

3. The optical fiber sheet according to claim 1,
   wherein the core diameter is 80 μm, the cladding thickness is 22.5 μm and the flexural rigidity of the optical fiber is 0.26 N·mm².

4. The optical fiber sheet according to claim 1,
wherein the core diameter is 50 μm, the cladding thickness is 37.5 μm and the flexural rigidity of the optical fiber is 0.14 N·mm$^2$.

5. The optical fiber sheet according to claim 1,
wherein the core diameter is 100 μm, the cladding thickness is 12.5 μm and the flexural rigidity of the optical fiber is 0.50 N·mm$^2$.

\* \* \* \* \*